US00PP22973P3

(12) United States Plant Patent
Austin

(10) Patent No.: US PP22,973 P3
(45) Date of Patent: Aug. 21, 2012

(54) ***ROSA HYBRIDA* SHRUB PLANT NAMED 'AUSPANIER'**

(50) Latin Name: *Rosa hybrida*
Varietal Denomination: AUSpanier

(75) Inventor: David C. H. Austin, Wolverhampton (GB)

(73) Assignee: David Austin Roses Ltd, Albrighton, Wolverhampton (GB)

( * ) Notice: Subject to any disclaimer, the term of this patent is extended or adjusted under 35 U.S.C. 154(b) by 23 days.

(21) Appl. No.: 13/065,163

(22) Filed: Mar. 14, 2011

(65) Prior Publication Data

US 2012/0096606 P1 Apr. 19, 2012

(30) Foreign Application Priority Data

Oct. 14, 2010 (QZ) ..... PBR 2010/2158

(51) Int. Cl.
*A01H 5/00* (2006.01)

(52) U.S. Cl. ..... Plt./107; Plt./102

(58) Field of Classification Search ..... Plt./102, Plt./107
See application file for complete search history.

*Primary Examiner* — Susan McCormick Ewoldt

(74) *Attorney, Agent, or Firm* — Kauth, Pomeroy, Peck & Bailey LLP

(57) ABSTRACT

A variety of rose plant of the shrub class, named 'AUSpanier'. The 'AUSpanier' rose is a plant having a large airy shrub with dainty gray-green foliage. The flowers of the plant are held on by thin, wiry stems and are a soft rose pink and semi-double in form that open to provide a camellia-like bloom. The fragrance of the rose is predominately myrrh, developing musk as the flower ages.

1 Drawing Sheet

Classification: The present invention relates to a new *Rosa hybrida* shrub.

Variety denomination: The new plant has the varietal denomination 'AUSpanier.'

CROSS-REFERENCE TO RELATED APPLICATIONS

The current application claims priority to a European Community Plant Variety Application No. 2010/2158, filed Oct. 14, 2010, the disclosure of which is incorporated herein by reference.

ORIGIN OF INVENTION

This invention relates to a new and distinct variety of shrub rose plant named 'AUSpanier', which was originated by crossing two unnamed, unpatented varieties of *Rosa hybrida*.

BACKGROUND OF THE INVENTION

The primary objective of this breeding was to produce a variety of rose which is a large airy shrub with dainty, grey-green foliage; flowers that are held on thin, wiry stems with a soft rose pink and semi-double form that open to provide a camellia-like bloom and that have a predominately myrrh fragrance; and a growth that has excellent disease resistance.

SUMMARY OF THE INVENTION

Among the features which distinguish the new variety from others presently available and commercial rose cultivars known to the inventor is the following combination of characteristics: dainty foliage, blooms of soft rose pink with a semi-double form, and a large airy shrub.

Asexual reproduction of the new variety by budding as performed outdoors at Bowling Green Lane in Albrighton, Britain shows that the foregoing and other distinguishing characteristics come true to form and are established and transmitted through succeeding asexual propagations. 'AUSpanier' may be asexually propagated by budding. The budding successfully occurred on the plant/rootstock *Rosa* cv. 'Dr. Huey' in the United States, and *Rosa dumetorum* cv. 'Laxa' for the observed plants in the UK.

COMPARISON WITH THE CLOSEST COMMERCIALLY AVAILABLE CULTIVAR

The closest commercially available cultivar to the new variety is the 'AUSoscar' (unpatented variety). The new rose may be distinguished from the 'AUSoscar' variety by the following combination of characteristics: the 'AUSoscar' shows a red ring around the stamens where the stamens attach to the calyx and there is a cream-colored area in the basal zone of the petals, whereas there are no such rings on the 'AUSpanier,' and the petals of 'AUSpanier' are a slightly deeper, more uniform pink. In addition, 'AUSoscar' also has more smaller, linear prickles, whereas the prickles on 'AUSpanier' are deep concave.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

The following description is of 1 year-old rose plants of the new variety grown outdoors in Albrighton, Britain in the month of July. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.5 cm long and 1.8 cm in diameter when the petals start to unfurl.

*Form*.—The bud form is short and pointed ovoid.

*Color*.—When sepals first divide, the bud color is red-purple RHS 67C. When half blown, the upper sides of the petals are red-purple RHS 67B, and the lower sides of the petals are red-purple RHS 68B.

*Calyx*.—Shape: star-shape, with sepals folding back over receptacle. Length: 4 cm. Diameter: 6.5 cm.

*Sepals*.—Arrangement: Regular. Color: Upper Surface: greyed-green RHS 194A with some red-purple RHS 60C. Lower Surface: yellow-green RHS 144B with red-purple RHS 60C. Length: 3 cm. Width: 7 mm. Shape: Lanceolate. Margin: N/A. Surface texture: Upper Surface: Downy. Lower Surface: Rough. Number: There are 3 normally appendaged sepals, and 2 unappendaged sepals with hairy edges.

*Receptacles*.—Color: yellow-green RHS 146B with red-purple RHS 60C. Shape: funnel. Size: slender, about 1 cm×0.6 cm. Surface: Smooth.

*Peduncle*.—Length: short, averaging about 6 cm. Surface: Glandular. Color: yellow-green RHS 146B. Strength: Normal.

Blooms:

*Size*.—Large, average open diameter is about 10 cm.

*Borne*.—Several together in small clusters of 4 to 6 blooms having flat shape.

*Stems*.—Strength: Normal, average length is about 30 cm. Diameter: 3 mm.

*Form*.—When first open, bloom is high centered. Permanence of bloom: flattens.

Petalage: Number of petals under normal conditions: 26.

*Color*.—The upper sides of the petals are red-purple RHS 68A. The reverse sides of the petals are red-purple RHS 68B, and the based of the petals has a green-yellow spot RHS 1C.

*Variegations*.—N/A.

*Discoloration*.—The general tonality at the end of the first day is red-purple RHS 68A, and at the end of the third day is red-purple 68B. Thereafter color fades slightly to RHS 68C.

*Fragrance*.—Moderate. Character of fragrance: myrrh, turning spicy musk.

Petals:

*Texture*.—Smooth.

*Size*.—Width: 3.8 mm. Length: 5 cm.

*Surface*.—Smooth.

*Shape*.—Obovate.

*Margin*.—Entire.

*Apex shape*.—Rounded.

*Base shape*.—Obcordate.

*Form*.—Tips slightly recurved.

*Arrangement*.—Informal.

*Petaloids*.—Number: About 7. Color: red-purple RHS 68A. Length: Variable between 10 mm to 30 mm. Width: Variable between 5 mm to 16 mm. Shape: Curled ovate "half-petal" shape. Margin: Mostly entire.

*Persistence*.—Petals drop off cleanly before drying.

*Lastingness*.—On the plant: Fair, about 5 days. As a cut flower: Not tested.

Reproductive parts:

*Stamens*.—Number: 120. Length: 1 cm.

*Anthers*.—Length: 3 mm. Color: yellow-orange RHS 15C. Arrangement: Regular around styles.

*Filaments*.—Color: yellow-orange RHS 15B. Length: 9 mm.

*Pollen*.—Color: yellow-orange RHS 15C.

*Pistils*.—Number: 15. Length: 4 mm.

*Styles*.—Color: green-white RHS 157C. Length: 3 mm.

*Stigmas*.—Color: green-white RHS 157C. Length: 1 mm.

*Hips*.—None Observed.

PLANT CHARACTERISTICS

Plant form: Shrub.

Plant growth: Medium.

Age to maturity: Two years.

Mature plant: Height: 1 m 35 cm. Width: 1 m.

Rootstock: *Rosa* cv. 'Dr. Huey' in the United States, *Rosa dumetorum* cv. 'Laxa' for the observed plants in the UK.

Foliage:

*Number*.—Leaflets on normal mid-stem leaves is: 5 (including terminal leaflet).

*Size*.—Small, about 13 cm long×8 cm wide.

*Quantity*.—Abundant. Number of leaves per flowering stem is: 10.

*Color*.—New foliage: Upper side: red-purple RHS 59A tinged with yellow-green RHS 146A. Lower side: red-purple RHS 59A tinged with yellow-green RHS 146A. Old foliage: Upper side: green RHS 137A. Lower side: yellow-green RHS 147B.

Leaflets:

*Size*.—About 4.4 cm long×2.8 cm wide.

*Shape*.—Broadly oval.

*Base shape*.—Obtuse.

*Apex shape*.—Cuspidate.

*Texture*.—Smooth.

*Edge*.—Serrated.

*Serrations*.—Single.

*Petiole*.—Color: green RHS 143A marked with red-purple RHS 59A. Length: Variable 2.5 to 4.5 cm. Width: 2 mm. Surface Texture: Smooth.

*Petiole rachis*.—Color: green RHS 143A, marked with red-purple RHS 59A. Underside: rough with some prickles.

*Stipules*.—Length: 3 cm, glandular and hairy. Color: green RHS 143B.

*Auricle*.—Shape: Narrow, sword-shaped. Length: 7 to 13 mm. Width: 1.5 mm. Color: green RHS 143B.

*Vein color*.—Same as leaf color.

*Venation pattern*.—Reticulate.

Wood:

*New wood*.—Color: red-purple RHS 59A. Bark: Smooth.

*Old wood*.—Color: light green RHS 143A. Bark: Smooth.

Branching habit:

*Number*.—7.

*Lateral branch dimensions*.—Length: 75 cm. Width: 6 mm.

Stems:

*Mature stem*.—Length: 80 cm. Diameter: 6 mm.

*Internode distance*.—8 cm. The above measurements are all variable, depending on growing conditions in a season.

*Stem pubescence present*.—No.

Prickles:

*Quantity*.—On main canes from base: Ordinary. Number per stem length: 6 per 10 cm. On laterals from main canes: Ordinary. Number per stem length: 10 per 10 cm.

*Form*.—Deep concave.

*Length*.—8 mm (Smaller prickles near the top of the plant, although shape and form remain the same).

*Color when young*.—Red-purple RHS 59A.

*Color when mature*.—Yellow-orange RHS 20D.

Small prickles:

*Quantity*.—Main stalk: Few. Number per stem length: 10 per 10 cm on top section (third) of stem. Laterals: Few. Number per stem length: 10 per 10 cm.

*Color*.—When young: red-purple RHS 59A. When mature: yellow-orange RHS 20D.

Disease resistance:

*Mildew*.—Resistant.

*Blackspot*.—Resistant.

*Rust*.—Resistant.

Pest resistance: Not tested.

Winter hardiness: Not tested.

Growing conditions: Normal.

What is claimed is:

1. A new and distinct variety of rose plant of the shrub class suitable for repeat flower production, substantially as herein shown and described.

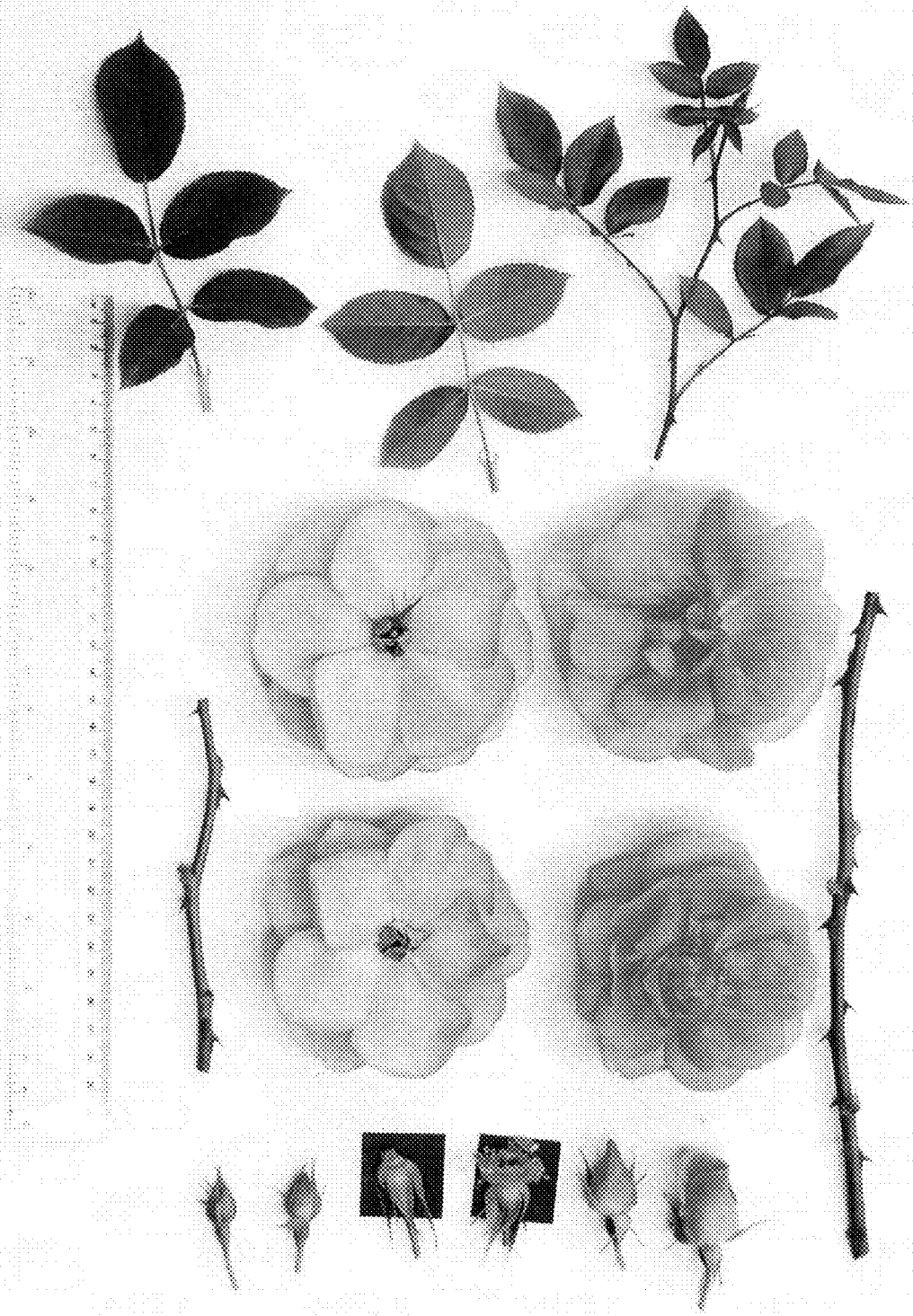

* * * * *